United States Patent
Jung et al.

(10) Patent No.: US 9,044,751 B2
(45) Date of Patent: Jun. 2, 2015

(54) GENE ANALYSIS DEVICE

(75) Inventors: Won-jong Jung, Seongnam-si (KR); Sun-ok Jung, Seongnam-si (KR); Won-seok Chung, Suwon-si (KR); Chin-sung Park, Yongin-si (KR); Joon-ho Kim, Seongnam-si (KR); Kak Namkoong, Seoul (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 0 days.

(21) Appl. No.: 13/608,533

(22) Filed: Sep. 10, 2012

(65) Prior Publication Data

US 2013/0137165 A1  May 30, 2013

(30) Foreign Application Priority Data

Nov. 30, 2011  (KR) ................. 10-2011-0127225

(51) Int. Cl.
   - *C12M 1/34*   (2006.01)
   - *C12M 3/00*   (2006.01)
   - *B01L 3/00*   (2006.01)
   - *G01N 21/64*   (2006.01)
   - *G01N 21/03*   (2006.01)
   - *G01N 21/05*   (2006.01)

(52) U.S. Cl.
   CPC ...... *B01L 3/502715* (2013.01); *G01N 21/6452* (2013.01); *G01N 2021/0314* (2013.01); *G01N 2021/0325* (2013.01); *G01N 2021/058* (2013.01); *G01N 2021/6463* (2013.01); *B01L 2300/0654* (2013.01); *B01L 2300/0816* (2013.01)

(58) Field of Classification Search
   CPC ............... B01L 2300/0654; B01L 2300/0816; B01L 3/502715; C12N 15/00; C12Q 1/68; G01N 2021/0314; G01N 2021/0325; G01N 2021/058; G01N 2021/6463; G01N 21/64; G01N 21/6452
   USPC ...................................... 435/287.2
   See application file for complete search history.

(56) References Cited

U.S. PATENT DOCUMENTS

| | | | |
|---|---|---|---|
| 2003/0157725 A1* | 8/2003 | Franzen et al. | 436/171 |
| 2004/0235205 A1* | 11/2004 | Levy et al. | 438/14 |
| 2008/0085552 A1* | 4/2008 | Larson et al. | 435/288.7 |
| 2008/0192254 A1 | 8/2008 | Kim et al. | |
| 2010/0271621 A1* | 10/2010 | Levy et al. | 356/73 |

FOREIGN PATENT DOCUMENTS

| | | |
|---|---|---|
| KR | 1020080074252 A | 8/2008 |
| KR | 1020090128891 A | 12/2009 |
| KR | 1020120036230 A | 4/2012 |

* cited by examiner

*Primary Examiner* — Nathan Bowers
*Assistant Examiner* — Lydia Edwards
(74) *Attorney, Agent, or Firm* — Leydig, Voit & Mayer, Ltd.

(57) ABSTRACT

A gene analysis device including an illumination optical system radiating exciting light onto a sample solution; a microfluidic device for forming a bio-reaction space of the sample solution and including at least one micro-chamber in which a reflection pattern is formed; and a detection optical system for detecting a fluorescence signal generated by a bio-reaction in the micro-chamber and comprising a photodetector.

15 Claims, 8 Drawing Sheets

GENE ANALYSIS DEVICE

CROSS-REFERENCE TO RELATED APPLICATIONS

This application claims the benefit of Korean Patent Application No. 10-2011-0127225, filed on Nov. 30, 2011, in the Korean Intellectual Property Office, the disclosures of which are incorporated herein in their entirety by reference.

BACKGROUND

As the age of point-of-care healthcare has come, the importance of gene analysis, external diagnosis, gene sequencing, etc. is being emphasized. Also, demand therefor is gradually increasing. Thus, a system capable of performing a large amount of tests by using only a small amount of samples has been developed and implemented. Also, in order to realize such a system, microfluidic devices such as a microfluidics chip or a lab-on-a-chip (LOC) have attracted much attention. The microfluidic device including a plurality of micro-channels and a plurality of micro-chambers is designed to control and manipulate tiny amounts of fluids, for example, amounts from several nl to several ml. By using the microfluidic device, a reaction time of microfluidics may be minimized, and reaction of the microfluidics and measurement of a result of the reaction may be performed at the same time. Such a microfluidic device may be manufactured in various ways, and various materials may be used according to a method of manufacturing the microfluidic device.

Meanwhile, for example, during a gene analysis process, in order to ascertain whether a certain deoxyribonucleic acid (DNA) exists in a sample or to exactly ascertain an amount of DNA, a process of refining/extracting an actual sample and then sufficiently amplifying the sample to be measured is required. From among various gene amplification methods, for example, a polymerase chain reaction (PCR) is most widely used. Also, fluorescence detection is mainly used as a method of detecting DNA amplified through PCR. For example, in quantitative real-time PCR (qPCR), a plurality of fluorescent dyes/probes and primer sets are used to amplify a target sample and to detect/measure the target sample in real time. For example, regarding the qPCR using a Taqman probe, the qPCR uses the Taqman probe that has fluorescence properties when separated from a template during amplification of DNA. In other words, as a PCR cycle progresses, a number of the Taqman probes separated from the templates exponentially increases, and thus a fluorescence signal level exponentially increases. Changes in the fluorescence signal level are measured by using an optical system to enable determination of presence of a target sample or quantitative analysis. As the PCR cycle progresses, a curve of a fluorescence signal level follows an S-curve, and a Ct (threshold cycle) value is set at a point where the fluorescence signal level sharply changes and the Ct value is measured. A platform, such as external diagnosis, gene analysis, development of a biomarker, or gene sequencing, to which a qPCR technology is applied, has already been commercialized.

In detecting a fluorescence signal by using a bio-reaction, such as a PCR, occurring in a microfluidic device using tiny amounts of fluid, e.g., from several nl to several ml, a signal level is generally proportional to an amount of sample solutions, and a detectable limitation is referred to as limit of detection (LOD). An amplifier may be used to raise a signal level, but in this case, noise is also amplified. Accordingly, an amplifier is not proper to detect a tiny amount of targets. Therefore, research on a method of improving LOD by minimizing a loss of a fluorescence signal is required.

SUMMARY

Provided is a gene analysis device capable of increasing an intensity of a fluorescence signal due to a bio-reaction.

Additional aspects will be set forth in part in the description which follows and, in part, will be apparent from the description, or may be learned by practice of the presented embodiments.

According to an aspect of the present invention, a gene analysis device includes an illumination optical system radiating exciting light onto a sample solution; a microfluidic device for forming a bio-reaction space of the sample solution and including at least one micro-chamber in which a reflection pattern is formed; and a detection optical system for detecting a fluorescence signal generated by a bio-reaction in the micro-chamber and including a photodetector.

The reflection pattern may have a retro-reflective structure in which light radiated by the illumination optical system and incident into the micro-chamber may be reflected in a light incidence direction.

A direction in which the light radiated by the illumination optical system is incident into the micro-chamber is in accordance with an optical axis of an optical path in which a fluorescence signal generated by the bio-reaction in the micro-chamber is directed to the detection optical system.

The reflection pattern may be formed on a surface perpendicular to the optical axis in the micro-chamber.

The reflection pattern may be formed on a bottom surface of the micro-chamber.

The microfluidic device may be formed of a material of a silicon substrate.

The reflection pattern may include mirror surfaces each having a predetermined inclination formed according to a direction of a crystal surface of silicon (Si) during wet-etching of Si.

The microfluidic device may be formed of a polymer material.

The reflection pattern may be formed by injection molding or hot-embossing.

The illumination optical system may include: a light source for emitting exciting light; a collimating lens for collimating exciting light emitted from the light source as parallel light; an objective lens for imaging the exciting light on the micro-chamber of the microfluidic device; and a beam splitter for reflecting or transmitting exciting light emitted from the light source to proceed toward the objective lens and for transmitting or reflecting a fluorescence signal generated by the micro-chamber to proceed toward the photodetector.

The illumination optical system may further include a first filter that is disposed between the collimating lens and the beam splitter and transmits only exciting light components with wavelengths for exciting fluorescent dyes included in the micro-chamber from among the light emitted from the light source.

The detection optical system may include: the objective lens; the beam splitter; and a photodetector for measuring an intensity of the fluorescence signal generated by the micro-chamber due to the exciting light.

The detection optical system may further include an imaging lens that is disposed between the beam splitter and the photodetector and images the fluorescence signal generated by the micro-chamber on the photodetector.

The detection optical system may further include: a second filter that is disposed between the beam splitter and the imaging lens and removes a fluorescence signal generated by another micro-chamber adjacent to the micro-chamber; and a third filter that is disposed between the second filter and the imaging lens and removes light having a component of the exciting light.

BRIEF DESCRIPTION OF THE DRAWINGS

These and/or other aspects will become apparent and more readily appreciated from the following description of the embodiments, taken in conjunction with the accompanying drawings of which.

DETAILED DESCRIPTION

Hereinafter, the present invention will be described in detail by explaining exemplary embodiments of the invention with reference to the attached drawings. The same reference numerals in the drawings denote the same element. In the drawings, the thicknesses of layers and regions are exaggerated for clarity.

Figure 1:
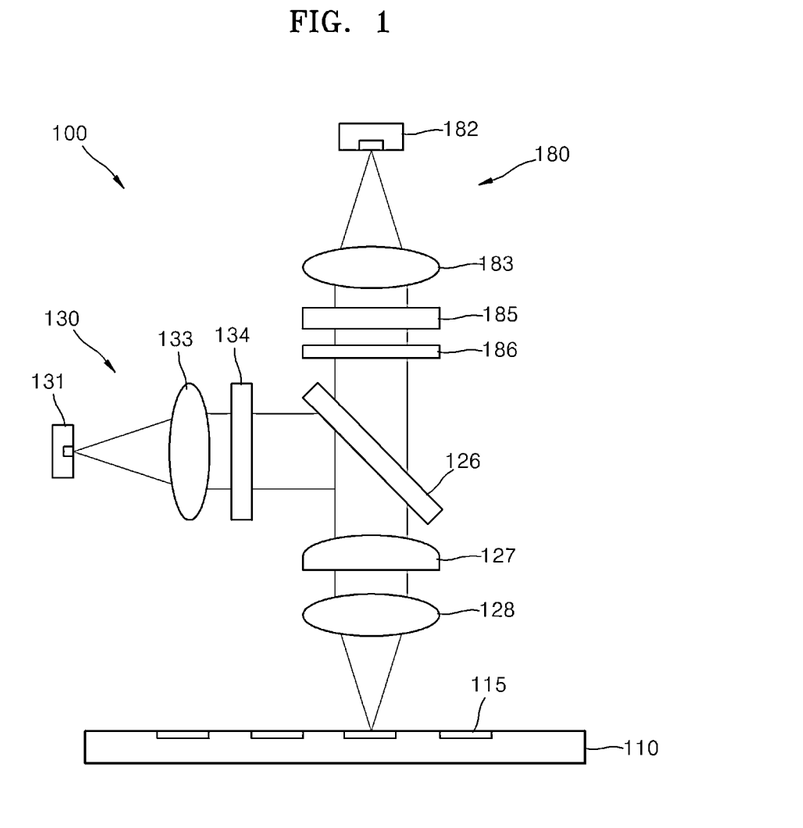
FIG. 1 is a schematic view showing an exemplary structure of a gene analysis device according to an embodiment of the present invention.
Figure 2:
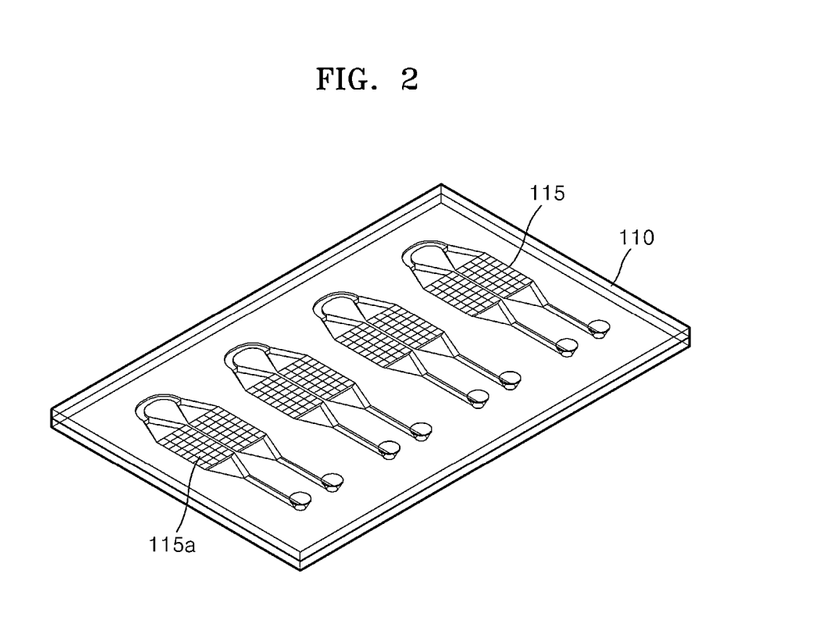
FIG. 2 is a view showing a detailed shape of a chamber of the microfluidic device included in the gene analysis device of FIG. 1.

FIG. 1 is a schematic view showing an exemplary structure of a gene analysis device 100 according to an embodiment of the present invention. FIG. 2 is a view showing a shape of a micro-chamber 115 of a microfluidic device 110 included in the gene analysis device 100 of FIG. 1.

Referring to FIG. 1, the gene analysis device 100 includes an illumination optical system 130 for radiating exciting light onto a sample solution, and a detection optical system 180. The gene analysis device 100 also includes the microfluidic device 110 for forming a bio-reaction space of the sample solution and including at least one micro-chamber 115 in which a reflection pattern is formed. A photodetector 182 can detect a fluorescence signal generated by a bio-reaction that occurs in the micro-chamber 115.

The illumination optical system 130 radiates light for exciting a fluorescence signal onto a sample solution to be tested, and includes a light source 131 that emits exciting light, a collimating lens 133 for collimating exciting light emitted from the light source 131 (i.e., making the exciting light rays parallel), an objective lens 128 for imaging and/or focusing exciting light on the micro-chamber 115 of the microfluidic device 110, and a beam splitter 126 for reflecting exciting light emitted from the light source 131 toward the objective lens 128 and transmitting a fluorescence signal generated by the micro-chamber 115 toward the photodetector 182.

Also, a first filter 134 may be further disposed between the collimating lens 133 and the beam splitter 126, wherein the first filter 134 transmits only exciting light components with wavelengths for exciting fluorescent dyes included in the micro-chamber 115 from among light emitted from the light source 131. A beam shaping lens 127 may be disposed between the beam splitter 126 and the objective lens 128, wherein the beam shaping lens 127 enlarges an optical spot size of the exciting light according to a shape of the micro-chamber 115.

In this regard, the light source 131 may be a light emitting diode (LED) or a laser diode (LD) that emits light with a wavelength of, for example, from about 400 nm to about 700 nm. In FIG. 1, for convenience of description, the collimating lens 133, the beam shaping lens 127, and the objective lens 128 are each shown as a single lens, but the collimating lens 133, the beam shaping lens 127, and the objective lens 128 each may include a plurality of lenses. Also, the first filter 134 may be, for example, a band-pass filter (BPF) that passes only light of a specific wavelength band.

The detection optical system 180 detects a fluorescence signal generated by the micro-chamber 115, and includes the beam splitter 126 that passes the fluorescence signal generated by the micro-chamber 115. The photodetector 182 measures an intensity of the fluorescence signal and converts the fluorescence signal into an electrical signal. Also, an imaging lens 183 for imaging and/or focusing the fluorescence signal generated by the micro-chamber 115 on the photodetector 182 may be further disposed between the beam splitter 126 and the photodetector 182. A second filter 186 for removing a fluorescence signal generated by another micro-chamber adjacent to the micro-chamber 115 may be further disposed between the beam splitter 126 and the imaging lens 183, and a third filter 185 for removing light having an exciting light component may be further disposed between the second filter 186 and the imaging lens 183. In the detection optical system 180, the objective lens 128 may convert a fluorescence signal generated by the micro-chamber 115 into parallel light, and the beam shaping lens 127 may transform an optical spot of the fluorescence signal generated by the micro-chamber 115 according to a shape of the photodetector 182. Accordingly, the illumination optical system 130 and the detection optical system 180 may share the beam splitter 126, the beam shaping lens 127, and the objective lens 128.

In this regard, the photodetector 182 may include, for example, an array of photodiodes, or may include a charge-coupled device (CCD) image sensor or a complementary metal oxide semiconductor (CMOS) image sensor. In FIG. 1, for convenience of description, the imaging lens 183 is shown as a single lens, but the imaging lens 183 may include a plurality of lenses. Meanwhile, the second filter 186 for preventing interference from an adjacent micro-chamber may be a high-pass filter (HPF) that only passes wavelength bands higher than a specific wavelength band. When measurement is not simultaneously performed with respect to a plurality of micro-channels but is performed only with respect to one micro-channel at a time, the second filter 186 may not be required. The third filter 185 may be, for example, a BPF that passes only light of a specific wavelength band.

In the embodiment described with reference to FIG. 1, it has been described that exciting light generated by the light source 131 is reflected by the beam splitter 126, and a fluorescence signal generated by the micro-chamber 115 passes the beam splitter 126. In other words, in the embodiment described with reference to FIG. 1, an optical path of the exciting light is bent nearly at a right angle by the beam splitter 126, and an optical path of the fluorescence signal has a straight line shape. However, in another embodiment, the beam splitter 126 may be designed to pass exciting light and reflect a fluorescence signal. In this case, an optical path of the exciting light has a straight line shape, and an optical path of the fluorescence signal may be bent nearly at a right angle. In other words, the beam splitter 126 may pass or reflect exciting light emitted from the light source 131 to proceed toward the objective lens 128 and may pass or reflect a fluorescence signal generated by the micro-chamber 115 to proceed toward the photodetector 182. As such, the beam splitter 126 for dividing the optical path of the exciting light and the optical path of the fluorescence signal may be a dichroic mirror that passes light of a specific wavelength and reflects light of all other wavelengths or reflects light of a specific wavelength and passes light of all other wavelengths.

The microfluidic device 110 is disposed to accurately analyze a sample according to various purposes, such as a clinical purpose, and includes at least one micro-chamber 115 used for a bio-reaction. As shown in FIG. 2, the microfluidic device 110 includes an inlet through which a sample solution enters in addition to the micro-chamber 115, and a reflection pattern 115a is formed in the micro-chamber 115. The reflection pattern 115a is formed to minimize a loss of a fluorescence signal formed by bio-reaction, and may have a retro-reflective structure in which light radiated by the illumination optical system 130 and incident into the micro-chamber 115 may be reflected in a light incidence direction. As shown in FIG. 1, a direction in which light radiated by the illumination optical system 130 is incident into the micro-chamber 115 may be in accordance with an optical axis of an optical path in which a fluorescence signal generated by a bio-reaction in the micro-chamber 115 is directed to the detection optical system 180. In this case, the reflection pattern 115a may be formed on a surface perpendicular to the optical axis in the micro-chamber 115. For example, the reflection pattern 115a may be formed on a bottom surface of the micro-chamber 115.

The microfluidic device 110 may be formed of a material of a silicon substrate. In this case, the reflection pattern 115a may be formed of mirror surfaces each having a predetermined inclination formed according to a direction of a crystal surface of silicon (Si) during wet-etching of Si. For example, tetramethylammonium hydroxide (TMAH), which is a Si etchant, has a characteristic that an etching rate varies according to the crystal surface of Si. An etching rate of Si (111) is particularly smaller than those of Si (100) and Si (110). Accordingly, when the microfluidic device 110 is formed of Si (100), a mirror surface having an inclination of about 54.7 degrees with respect to a bottom surface of the micro-chamber 115 is formed during wet etching using TMAH.

Figure 3A:
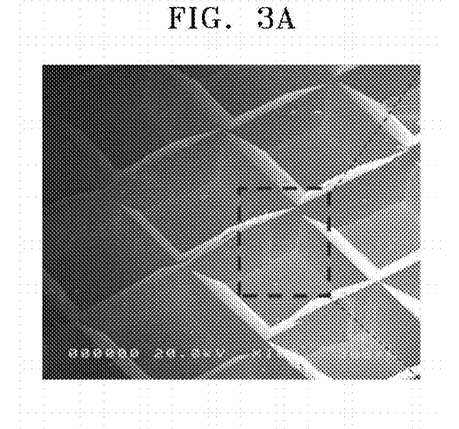
FIG. 3A is a photomicrograph of a reflection pattern formed in a chamber of the microfluidic device of FIG. 2.
Figure 3B:
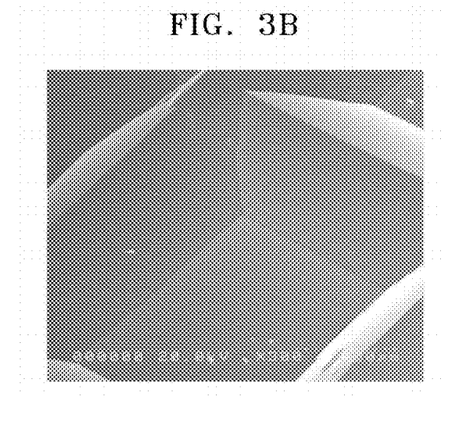
FIG. 3B is an enlarged photomicrograph of a part of the reflection pattern of FIG. 3.
Figure 4A:
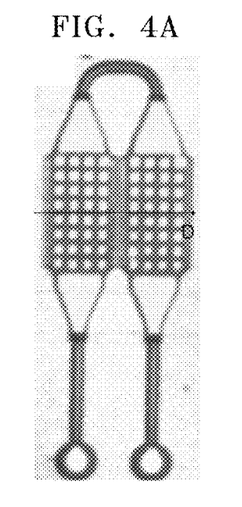
FIGS. 4A to 4D are photomicrographs of a microfluidic device showing a case where reflection patterns are formed in two chambers, a case where a reflection pattern is formed only in a left chamber, a case where a reflection pattern is formed only in a right chamber, and a case where a reflection pattern is not formed, respectively.
Figure 4B:
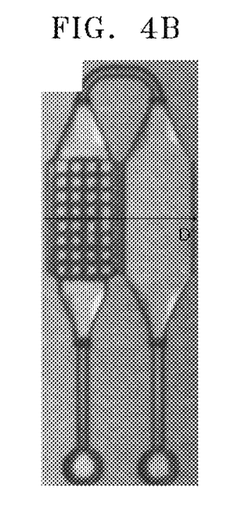
Figure 4C:
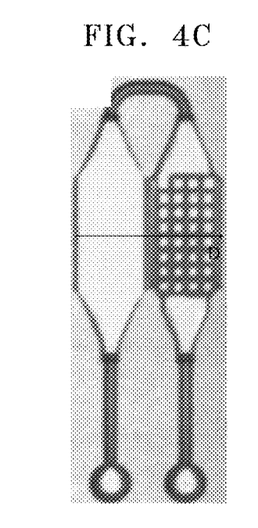
Figure 4D:
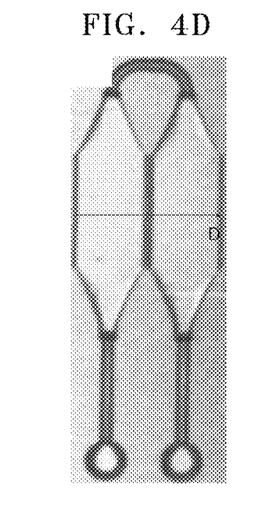
Figure 5A:
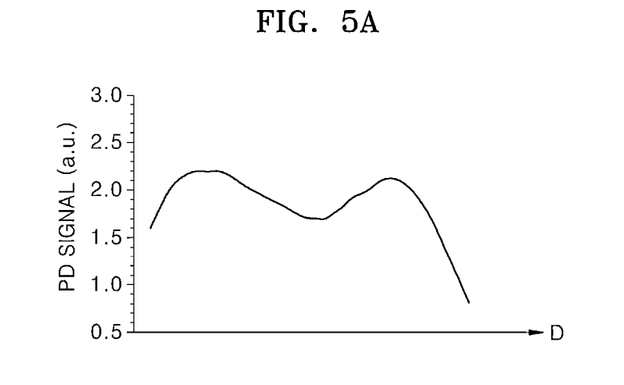
FIGS. 5A to 5D are graphs showing fluorescence signals associated with FIGS. 4A to 4D, respectively.
Figure 5B:
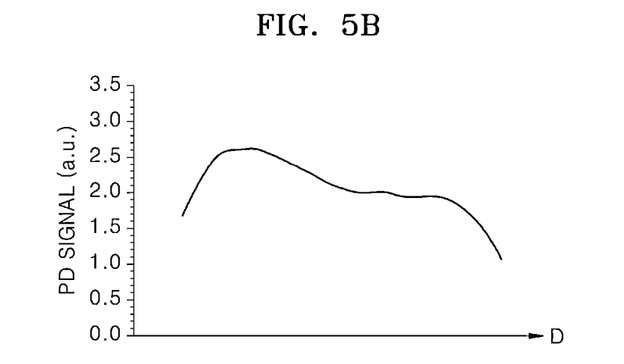
Figure 5C:
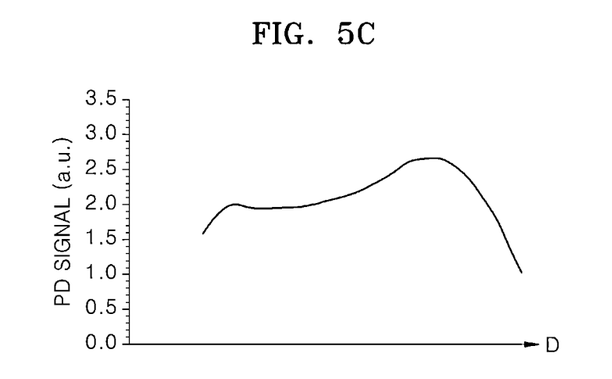
Figure 5D:
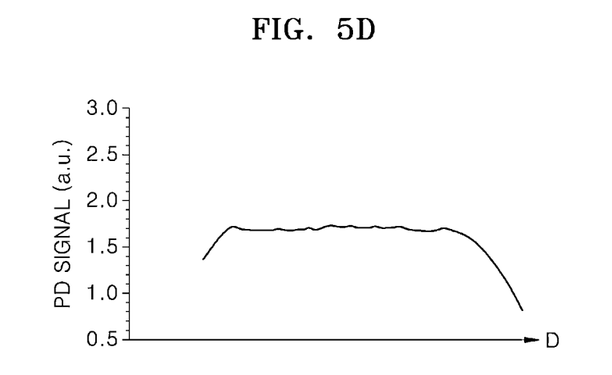

FIG. 3A is a photomicrograph of the reflection pattern 115a formed in the micro-chamber 115 of the microfluidic device 110 of FIG. 2, and FIG. 3B is an enlarged photomicrograph of a part of the reflection pattern 115a of FIG. 3.

The mirror surface formed in the micro-chamber 115 reduces a loss that may occur when fluorescence excited by light radiated by the illumination optical system 130 is incident on the detection optical system 180 and increases an intensity of a fluorescence signal to be detected. Potassium hydroxide (KOH), ethylenediamine procatechol (EDP), or the like may be used in addition to or as an alternative to TMAH as the Si etchant. By designing a mask in consideration of a final etching depth, the reflection pattern 115a may be formed through a single wet etching process without performing an additional process. The reflection pattern 115a may have any of various shapes and is not limited to the shape shown in FIG. 3A.

The microfluidic device 110 may be formed of a polymer material. In this case, a reflection pattern 115a having a described shape may be formed in the bottom surface of the micro-chamber 115 by injection molding, hot-embossing, or the like.

The inventor experimentally ascertained an intensity of a fluorescence signal increasing due to a reflection pattern. FIGS. 4A to 4D are photomicrographs of a microfluidic device used in the experiment. FIGS. 4A to 4D show a case where reflection patterns are formed in two chambers, a case where a reflection pattern is formed only in a left chamber, a case where a reflection pattern is formed only in a right chamber, and a case where a reflection pattern is not formed, respectively.

A configuration of a PCR solution and information regarding a target template, which are used in an experiment for measuring a fluorescence signal, are as follows.

TABLE

| PCR sol | |
|---|---|
| component | volume |
| Enzyme | 1 ul |
| 10x buffer | 25 ul |
| dNTP | 20 ul |
| Sa442(probe/primer mix) | 2.5 ul |
| Globulin(probe/primer mix) | 3 ul |
| Hu gDNA | 9.5 ul |

Target genes are Sa442 and globulin, and a result of PCR was measured by using Texas red (TR) dyes for globulin and FAM dyes for Sa442.

FIGS. 5A to 5D are graphs showing fluorescence signals with regard to FIGS. 4A to 4D, which were scanned over two chambers in a direction of an arrow D, respectively. Referring to FIGS. 5A to 5D, when a reflection pattern is formed, a level of the fluorescence signal is high.

Figure 6:
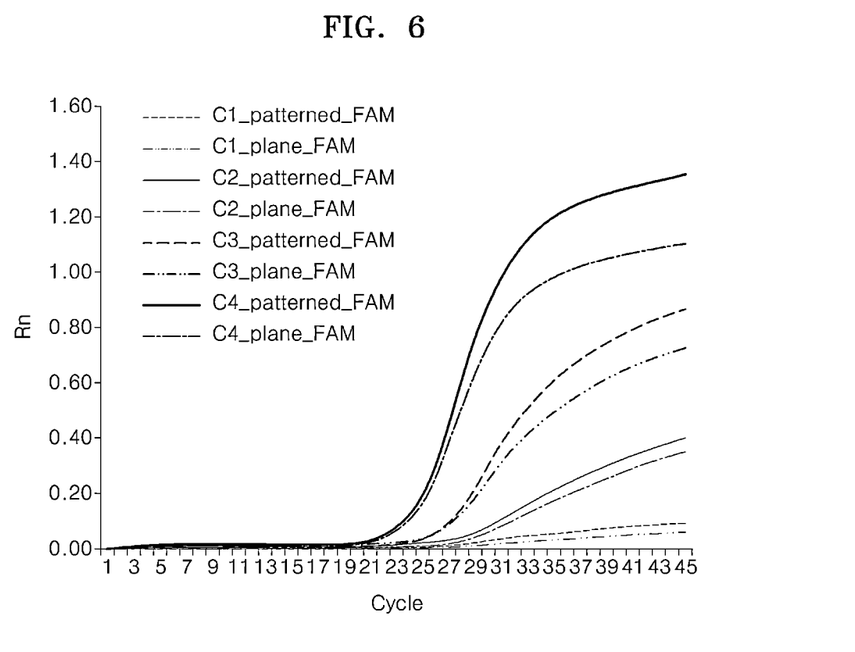
FIG. 6 is a graph showing an intensity of a fluorescence signal versus a PCR cycle according to a presence of a reflection pattern and a concentration of Sa442 according to an embodiment of the present invention.

FIG. 6 is a graph showing an intensity of a fluorescence signal versus a PCR cycle according to presence of a reflection pattern and a concentration of Sa442 according to an embodiment of the present invention.

In an experiment, Sa442 has concentrations $10^1$ copy/ul (C1), $10^2$ copy/ul (C2), $10^3$ copy/ul (C3), and $10^4$ copy/ul (C4). Regarding globulin, a PCR was performed by using the same concentration in all tests as an internal control. In the graph shown in FIG. 6, C1_patterned_FAM denotes a FAM fluorescence signal in a chamber having a reflection pattern when the concentration of the Sa442 is C1, and C1_plane_FAM denotes a FAM fluorescence signal in a chamber not having a reflection pattern when the concentration of Sa442 is C1. Referring to PCR curves, as the concentration of Sa442 is increased, an intensity of the measured FAM fluorescence signal is increased. Also, in the same concentration of Sa442, when the reflection pattern is formed, the intensity of the fluorescence signal is relatively high.

Table 2 shows intensities of a fluorescence signal at a 45th cycle of FIG. 6 with respect to concentrations.

TABLE 2

| Concentration | Rn_F_pattern | Rn_F_plane | ΔRn_F | ΔRn_F(%) |
|---|---|---|---|---|
| C1 | 0.093 | 0.060 | 0.033 | 55.0 |
| C2 | 0.400 | 0.351 | 0.049 | 15.0 |
| C3 | 0.865 | 0.726 | 0.139 | 19.1 |
| C4 | 1.349 | 1.103 | 0.234 | 22.3 |

The Rn_F_pattern and Rn_F_plane show intensities of the fluorescence signal of the 45th cycle when a reflection pattern is formed and when a reflection pattern is not formed, respectively. ΔRn_F shows a difference in intensities of the fluorescence signal according to the presence of the reflection pattern.

Referring to Table 2, as a concentration is increased, an intensity of the fluorescence signal is increased. In the same concentration, when the reflection pattern is formed, the intensity of the fluorescence signal is relatively high. A degree by which the intensity of the fluorescence signal by the reflection pattern is increased is more apparent at a low concentration of Sa442.

The inventor also measured a Ct value according to the presence of the reflection pattern. Regarding the Ct value, as the PCR cycle progresses, a curve of the intensity of the fluorescence signal follows an S-curve, which shows a number of cycles at a point where the intensity of the fluorescence signal sharply changes. The inventor observed that when the reflection pattern is present, the fluorescence signal is high (relative to when the reflection pattern is absent) but the Ct value is not significantly different. However, in the experiment, the volume of solution in a micro-chamber having a reflection pattern, that is, the volume of solution used in the PCR, is smaller than the volume of solution in a micro-chamber not having a reflection pattern, by about 0.250 ul. This difference in volume of solution may affect the Ct value. Considering that even though a sample solution having a smaller volume is used in the PCR in a micro-chamber having a reflection pattern, the intensity of the fluorescence signal of the micro-chamber having a reflection pattern is higher than that of the micro-chamber not having a reflection pattern. If the solution used in the PCR has the same volume, it is expected that the Ct value is smaller when the reflection pattern is formed in the micro-chamber. Accordingly, the reflection pattern formed in the micro-chamber may result in an increase in performance of LOD. When the reflection pattern is formed in the micro-chamber, it may be more advantageous to react a tiny amount of bio-samples.

In the above-described embodiment, a shape of a microfluidic device and a shape of a reflection pattern formed in the micro-chamber have been described in detail. However, this is just an example, and the shapes of the microfluidic device and the reflection pattern may be modified in various ways. For example, a number of chambers included in the microfluidic device, positions and shapes of a fluid inlet and a fluid outlet, a structure of a micro-channel, and the like may be modified in various ways. Also, the reflection pattern formed in the micro-chamber may have various types of reflection structures in which a fluorescence signal generated due to exciting light incident into the micro-chamber may be incident on a detection optical system with minimum loss.

It should be understood that the exemplary embodiments described herein should be considered in a descriptive sense only and not for purposes of limitation. Descriptions of features or aspects within each embodiment should typically be considered as available for other similar features or aspects in other embodiments.

What is claimed is:

1. A gene analysis device comprising:
   a microfluidic device comprising a bio-reaction space including at least one micro-chamber for containing a sample solution, wherein a reflection pattern is located in the micro-chamber and positioned to contact the sample solution when present in the micro-chamber;
   an illumination optical system configured to radiate excitation light onto the micro-chamber; and
   a detection optical system comprising a photodetector configured to detect a fluorescence signal generated by a bio-reaction in the micro-chamber,
   wherein the reflection pattern is located on a bottom surface of the micro-chamber and has a retro-reflective structure in which light radiated by the illumination optical system and incident onto the micro-chamber is reflected in a light incidence direction.

2. The gene analysis device of claim 1, wherein a direction in which the light radiated by the illumination optical system is incident to the micro-chamber is in accordance with an optical axis of an optical path in which a fluorescence signal generated by the bio-reaction in the micro-chamber is directed to the detection optical system.

3. The gene analysis device of claim 2, wherein the reflection pattern is located on a surface of the micro-chamber and extends perpendicular to the optical axis.

4. The gene analysis device of claim 1, wherein the microfluidic device comprises a silicon substrate comprising the micro-chamber.

5. The gene analysis device of claim 4, wherein the reflection pattern comprises mirror surfaces each having a predetermined inclination defined by a direction of a crystal surface of silicon during wet-etching of silicon.

6. The gene analysis device of claim 1, wherein the microfluidic device comprises a polymer material.

7. The gene analysis device of claim 6, wherein the reflection pattern is defined by injection molding or hot-embossing.

8. The gene analysis device of claim 1, wherein the illumination optical system comprises:
   a light source for emitting exciting light;
   a collimating lens configured to collimate exciting light emitted from the light source;
   an objective lens configured to focus exciting light emitted from the light source on the micro-chamber of the microfluidic device; and
   a beam splitter configured to reflect or transmit exciting light emitted from the light source toward the objective lens, and transmit or reflect the fluorescence signal generated by the micro-chamber toward the photodetector.

9. The gene analysis device of claim 8, wherein the illumination optical system further comprises a first filter that is disposed between the collimating lens and the beam splitter and transmits only exciting light components with wavelengths for exciting fluorescent dyes included in the micro-chamber from among the light emitted from the light source.

10. The gene analysis device of claim 8, wherein the detection optical system and the illumination optical system share the same objective lens and beam splitter.

11. The gene analysis device of claim 10, wherein the detection optical system further comprises an imaging lens that is disposed between the beam splitter and the photodetector, which is configured to focus the fluorescence signal generated by the micro-chamber on the photodetector.

12. The gene analysis device of claim 11, wherein the detection optical system further comprises:
   a second filter that is disposed between the beam splitter and the imaging lens and configured to remove a fluorescence signal generated by a second micro-chamber adjacent to the micro-chamber; and
   a third filter that is disposed between the second filter and the imaging lens and is configured to remove light having a component of the exciting light.

13. The gene analysis device of claim 1, wherein the micro-chamber has a bottom surface facing the illumination optical system, and the reflection pattern is on the bottom surface of the microchamber.

14. The gene analysis device of claim 10, wherein the reflection pattern has a crosshatching pattern.

15. The gene analysis device of claim 10, wherein the microchamber is in a silicon substrate, and the reflection pattern comprises mirror surfaces each having a predetermined inclination defined by a direction of a crystal surface of silicon during wet-etching of silicon.

* * * * *